United States Patent [19]

Lambert

[11] Patent Number: 5,042,468
[45] Date of Patent: Aug. 27, 1991

[54] BREATHING DEVICE

[75] Inventor: Hans Lambert, Stockholm, Sweden

[73] Assignee: Gibeck Respiration AB, Upplands Vasby, Sweden

[21] Appl. No.: 476,984

[22] Filed: Feb. 8, 1990

[30] Foreign Application Priority Data

Feb. 13, 1989 [SE] Sweden ................ 8900484

[51] Int. Cl.$^5$ .............................................. A61H 9/00
[52] U.S. Cl. ............................ 128/200.26; 128/200.24; 128/207.29
[58] Field of Search .............. 128/200.24, 200.26, 128/207.14, 207.29, 911, 912

[56] References Cited

U.S. PATENT DOCUMENTS

| | | | |
|---|---|---|---|
| 3,066,674 | 12/1962 | Capra | 128/207.16 |
| 3,330,271 | 7/1967 | Hozier | 128/207.14 |
| 3,920,009 | 11/1975 | Olsen | 128/201.13 |

FOREIGN PATENT DOCUMENTS 348643  11/1970  Sweden .

Primary Examiner—Edgar S. Burr
Assistant Examiner—Lisa E. Malvaso
Attorney, Agent, or Firm—Henry R. Lerner

[57] ABSTRACT

A breathing device for tracheotomy patients, comprising a holder (12) detachably connected to the outer end of a tracheal cannula (11) or to a stoma in the patient's throat, the holder holding detachably a regenerative heat-moisture exchanger (14). The holder (12) is an air-proof receptacle having a first opening (12a) communicating with the outer end (11b) of the tracheal cannula (11) or with the stoma in the throat and a second opening (12b) situated opposite the first opening. The heat-moisture exchanger (14), which is provided with a filter body (16), sealingly engages with the edges of the second opening.

11 Claims, 1 Drawing Sheet

BREATHING DEVICE

DESCRIPTION

1. Technical field

The present invention relates to a breathing device for tracheotomy patients. The device comprises a holder detachably connected to the outer end of a tracheal cannula or to the stoma made in the patient's throat, the holder holding detachably a regenerative heat-moisture exchanger.

2. Background art

The need for warming and moisturizing the inspiration air in connection with the upper air passages being cut off as a result of tracheotomy is well known and several devices intended to fill this need have been proposed.

A known device of the above-mentioned kind is disclosed in SE-B 348 643 wherein a hold is detachably mounted to the cannula, the holder holding detachably a tube in which a regenerative heat-moisture exchanger body is disposed.

A disadvantage of the device according to the above-mentioned publication is that the device protrudes quite a bit from the patient's throat, which particularly to active people carrying the device poses a problem with respect to the risk of their accidentally touching the device, which might then be displaced of cause pain in the patient's throat, as well from the aesthetic point of view. Further disadvantages are the relatively complicated structure of the device and the insufficient tightness between the holder and the heat-moisture exchanger body.

A further example of a known device of the above-mentioned kind is disclosed in SE-B 385 767 wherein a bandage containing, among others, a heat-moisture exchanger filter is applied directly around the stoma made in the patient's throat.

A disadvantage of the last-mentioned device is that the bandage must be detached from the patient's throat every time the filter has to be changed, which sometimes has to be done several times a day. The change causes discomfort and often strain and harm to the skin, especially if this has previously been subject to radiation treatment. Furthermore, on each change not only the filter but also other parts of the bandage must be discarded, which is uneconomical.

DESCRIPTION OF THE INVENTION

It is an object of the present invention to eliminate the disadvantages of previously known devices of the above-mentioned kind and to provide a device which protrudes only a short distance from the patient's throat, is of simple construction, provides effective sealing between the patient's throat and the heat-moisture exchanger, allows the heat-moisture exchanger to be replaced without discomfort or harm to the patient and also without parts of the device other than the heat-moisture exchanger having to be discarded, and is formed in such a way as to allow the use of identical heat-moisture exchangers irrespectively of a tracheal cannula being inserted into the patient's throat or the device being connected directly to the stoma in the throat.

This object is achieved by the device according to the invention having been given the features stated in the characterizing portions of the claims.

PREFERRED EMBODIMENTS

Figure 1:
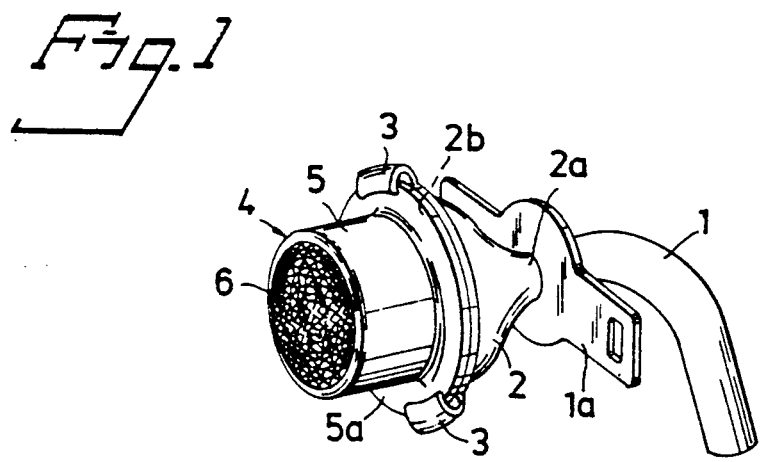
FIG. 1 is a perspective view of a first embodiment of the device according to the invention.
Figure 2:
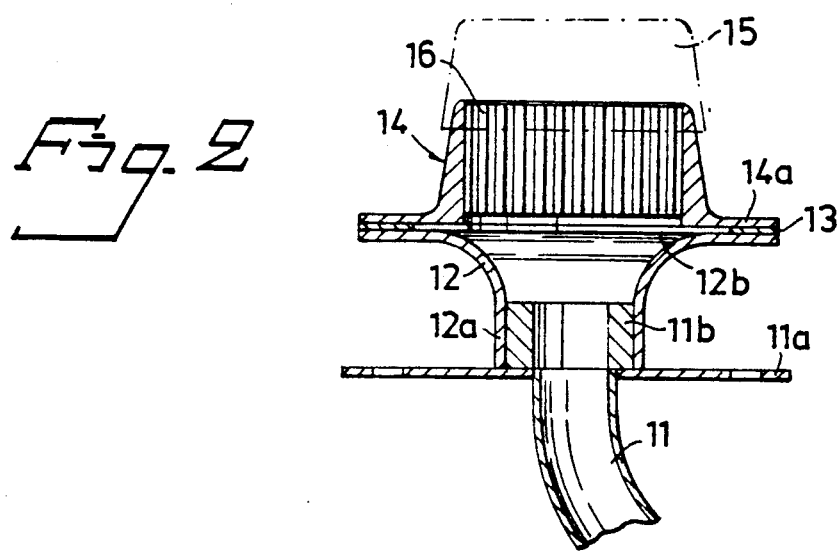
FIG. 2 is a sectional view of a second embodiment of the device according to the invention.
Figure 3:
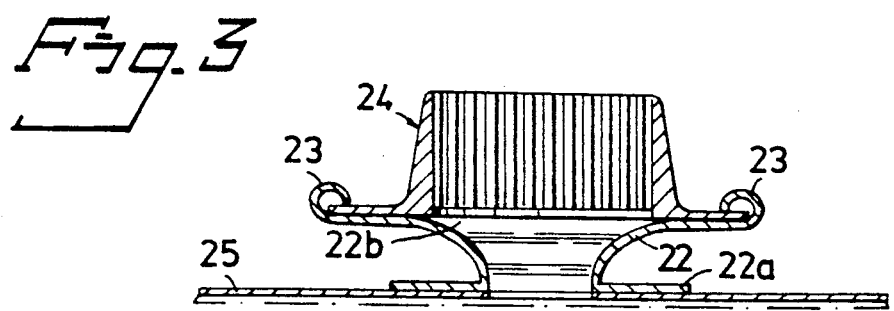
FIG. 3 is a sectional view of a third embodiment of the device according to the invention.

The breathing device shown in FIGS. 1 and 2 comprises a conventional tracheal cannula intended to be inserted through the stoma in the patient's throat for communication with the patient's windpipe, whereas the breathing device of FIG. 3 does not present such a cannula and is intended to be located over said stoma in the throat.

The tracheal cannula depicted in FIG. 1 is provided with an outer end which is formed as a slightly conical tube surrounded by a flange 1a. A holder 2 in the form of a funnel-shaped, air-proof receptacle has a slightly conical connection piece 2a which is insertable into the outer end of the cannula 1 into which it fits. Opposite the connection piece 2a the holder is provided with an opening 2b which is wider than the opening 2a of the connection piece, flexible holding means in the form of two claws 3 being attached to the edges of the opening 2b. The claws are integral with the holder 2 which is suitably made of a transparent plastic material.

A regenerative heat-moisture exchanger 4 is detachably mounted to the holder 2. The heat-moisture exchanger 4 comprises a cap-shaped plastic cover 5 containing a cylindrical, flat filter body 6 made up of helically wound strips of corrugated mini cardboard suitably impregnated with a hygroscopical material for good heat and moisture absorption from the expiration air and good heat and moisture emission to the inspiration air. The channels formed between the layers of corrugated cardboard run parallel to the central connecting line between the openings 2a and 2b. Instead of wound strips, the filter body 6 can be made up of cotton wool, foamed plastic or the like with substantially the same properties as the wound strips. In relation to its diameter, the filter body 6 has a low height. The filter body 6 suitably has a diameter of 24 mm and a height of 8 mm.

The heat-moisture exchanger 4 is attached to the holder 2 in one simple operation by pressing the cover 5 against the claws 3, which will then be displaced radially outwards and will snap over the flange 5a of the cover such that the latter will sealingly engage with the edges of the opening 2b. The heat-moisture exchanger 4 is removed in one simple operation by pulling it away from the holder 2, th claws 3 springing outwards thereby releasing the flange 5a.

FIG. 2 shows a tracheal cannula 11 the outer end of which is formed as a slightly conical tube 11b with a flange 11a attached to it. A holder 12 in the form of a funnel-shaped air-proof receptacle is provided with a slightly conical connection piece 12a, which fits onto the tube 11b of the cannula 11. On the holder 12, opposite the connection piece 12a, there is an opening 12b which is wider than the opening of the connection piece 12a, the edges of the opening 12b being perpendicular to the longitudinal axis of the connection piece 12a.

A regenerative heat-moisture exchanger 14 including filler body 16 is attached to the holder 12 and is identical to the heat-moisture exchanger 4 shown in FIG. 1. The exchanger 14 is detachably mounted to the holder 12 by adhesive means 13 between the edges of the opening 12b and the flange 14a of the exchanger 14. The adhesive means 13 can consist of, for example a suitable glue or double adhesive tape.

FIG. 2 is a diagrammatical view of a conventional speech valve 15 detachably mounted to the end of the exchanger 14 turned away from the holder 12. Alternatively, such a speech valve could be mounted to the heat-moisture exchanger of the devices according to the other embodiments.

FIG. 3 shows a holder 22 in the form of a funnel-shaped air-proof receptacle, said holder being provided with an opening surrounded by a circular flange 22a and a wider opening 22b opposite the first-mentioned opening and surrounded by edges parallel with the flange 22a.

A regenerative heat-moisture exchanger 24 is mounted to the holder 22 and identical to the heat-moisture exchangers 4 and 14 shown in FIGS. 1 and 2. The exchanger 24 is detachably mounted to the holder 22 by means of claws 23 which are identical to the claws 3 of FIG. 1, as shown if FIG. 3, or by adhesive means of the kind shown and described above in connection with FIG. 2.

At the end of the flange 22a turned away from the exchanger 24 there is attached an annular double adhesive tape 25. On removal of a protective sheet from the end of the tape 25 turned away from the exchanger 24, the device is attached in accordance with FIG. 3 around the stoma made in the patient's throat to the windpipe such that the central opening of the annular tape 25 will be right opposite the stoma in the throat and such that the tape will adhere around the stoma in the throat. Instead of the tape 25 it is possible to apply adhesive means of other suitable kind to the flange 22a.

in the devices described above and depicted in the figures, the devices protrude a comparatively short distance from the throat of the person carrying the same. On the holders 2, 12 and 22 there is, on each of them, a short distance between the two openings of the holder which is shorter than the extension of the holder perpendicularly thereto and is suitably less than the thickness of the exchangers 4, 14 and 24 respectively. For all three holders 2, 12 and 22 identical heat-moisture exchangers 4, 14 and 24 are used, which provides flexibility in use as well as cost savings.

Although some embodiments of the device according to the invention have been described above and shown on the drawings, it should be understood that the invention is not limited to said embodiments but only by the statements of the claims.

What I claim is:

1. A breathing device for tracheostomy patients, comprising:
    (a) a holder to be detachably connected to an outer end of a trachea cannula terminating at the throat of the patient or to a stoma in the patient's throat,
    (b) a regenerative heat-moisture exchanger including a filter body and held by said holder,
    (c) said holder being formed as an air-proof receptacle having
       (d) (1) a first opening communicating with the outer end of the tracheal cannula or with the stoma in the throat, and
       (d) (2) a second opening situated opposite the first opening,
    (e) the heat-moisture exchanger sealingly and detachably engaging with the edges of said second opening, and
    (f) said first and second holder openings being substantially axially aligned
    wherein the filter body is cylindrical, having passageways for breathing-air flowing towards and from the filter body substantially in parallel with a connecting line between the two openings, the distance between the openings being smaller than the extension of the filter body perpendicular to said connecting line.

2. A breathing device according to claim 1, wherein the receptacle is funnel-shaped, the two openings of said receptacle being circular and the second opening being wider than the first opening.

3. A breathing device according to claim 1, wherein the detachable connection between the filter body and the edges of the second opening comprises resilient holding means attached to said edges.

4. A breathing device according to claim 1, wherein the detachable connection between the stoma in the throat and the holder is an adhesive means.

5. A breathing device according to claim 1, wherein the detachable connection between the tracheal cannula and the holder comprises connection pieces being insertable into each other.

6. A breathing device according to claim 1, wherein a speech valve is detachably mounted to the heat-moisture exchanger on the side of the same which is turned away from the holder.

7. A breathing device according to claim 1, wherein the distance between the first opening and the second opening is shorter than the dimension of the holder perpendicularly thereto.

8. A breathing device according to claim 1, wherein the detachable connection between the filter body and the edges of the second opening comprises an adhesive means.

9. A breathing device according to claim 1, wherein the detachable connection between the tracheal cannula and the holder comprises adhesive means.

10. A breathing device for tracheotomy patients, comprising
    (a) a holder to be detachably connected to a stoma in the patient's throat,
    (b) a regenerative heat-moisture exchanger including a filter body and held by said holder,
    (c) said holder being formed as an air-proof receptacle having
       (d) (1) a first opening communicating with the stoma in the throat, and
       (d) (2) a second opening situated opposite the first opening,
    (e) the heat-moisture exchanger sealingly and detachably engaging with the edges of said second opening, and
    (f) said first and second holder openings being substantially axially aligned, 11. A breathing device according to claim 1, wherein the distance between the outer end of the stoma in the throat and the outermost surface of the exchanger is no greater than the diameter of the filter body which is cylindrical and which is perpendicular to the patient's throat.

* * * * *